United States Patent [19]

Hughes

[11] Patent Number: 5,221,740
[45] Date of Patent: Jun. 22, 1993

[54] OXEPANE ISOMERS OF RAPAMYCIN USEFUL AS IMMUNOSUPPRESSIVE AGENTS

[75] Inventor: Philip F. Hughes, Chapel Hill, N.C.

[73] Assignee: American Home Products Corporation, New York, N.Y.

[21] Appl. No.: 822,171

[22] Filed: Jan. 16, 1992

[51] Int. Cl.$^5$ ................. C07D 498/16; A61K 31/395
[52] U.S. Cl. ................................................. 540/456
[58] Field of Search ........................................ 540/456

[56] References Cited

U.S. PATENT DOCUMENTS

| | | | |
|---|---|---|---|
| 3,929,992 | 12/1975 | Sechal et al. | 540/456 |
| 5,091,389 | 2/1992 | Ondeyka et al. | 514/291 |
| 5,100,899 | 3/1992 | Calne | 514/291 |

OTHER PUBLICATIONS

Can. J. Physiol. Pharmacol. 55,48 (1977).

Primary Examiner—Robert T. Bond
Attorney, Agent, or Firm—Walter Patton

[57] ABSTRACT

A derivative of rapamycin of general formula (I)

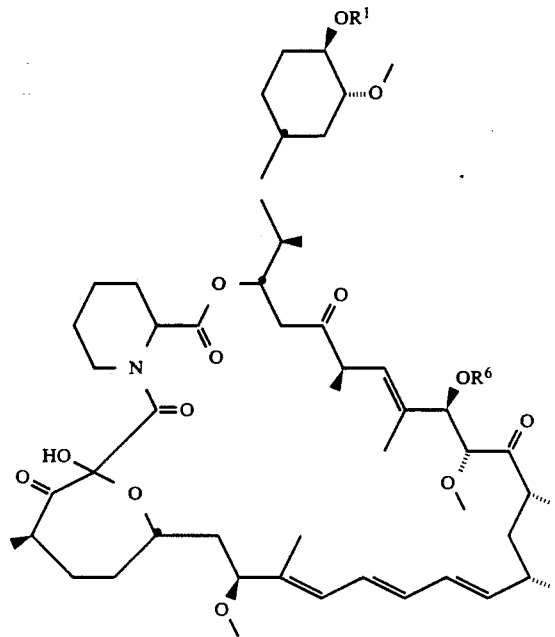

wherein $R^1$ and $R^2$ are selected from the group consisting of hydrogen, acyl, sulfonyl or alkyl or a pharmaceutically acceptable salt thereof, which is by virtue of its immunosuppressive activity is useful in treating transplantation rejection host vs. graft disease, autoimmune diseases, and diseases of inflammation.

5 Claims, No Drawings

OXEPANE ISOMERS OF RAPAMYCIN USEFUL AS IMMUNOSUPPRESSIVE AGENTS

BACKGROUND OF THE INVENTION

This invention relates to oxepane isomers of rapamycin and a method for using them in the treatment of transplantation rejection, host vs. graft disease, autoimmune diseases, diseases of inflammation, solid tumors, and fungal infections.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. Nos. 3,922,992; and 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1976) disclosed that rapamycin is effective in the experimental allergic encephalomyelitis model, a model for multiple sclerosis; in the adjuvant arthritis model, a model for rheumatoid arthritis; and effectively inhibited the formation of IGE-like antibodies.

The immunosuppresive effects of rapamycin have been disclosed in FASEB 3, 3411 (1989). Rapamycin has been shown to be effective in inhibiting transplant rejection (U.S. patent application Ser. No. 362,544 filed Jun. 6, 1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions.

DESCRIPTION OF THE INVENTION

This invention relates to compounds of general formula I

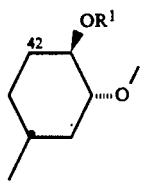

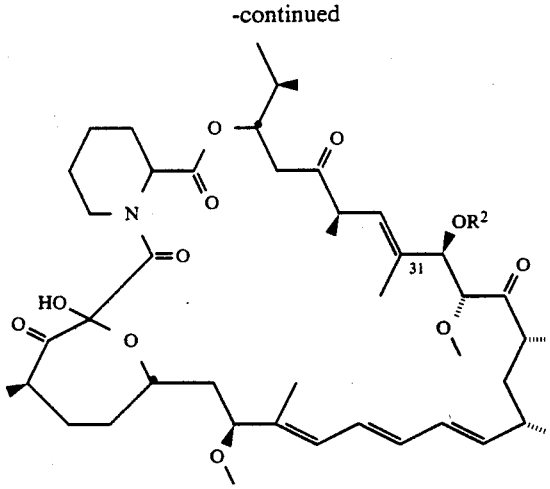

wherein $R^1$ and $R^2$ are selected from the group consisting of hydrogen, acyl, sulfonyl or alkyl or a pharmaceutically acceptable salt thereof.

The compounds of the present invention are oxepane isomers of rapamycin and its derivatives represented in the pyran form by the formula II

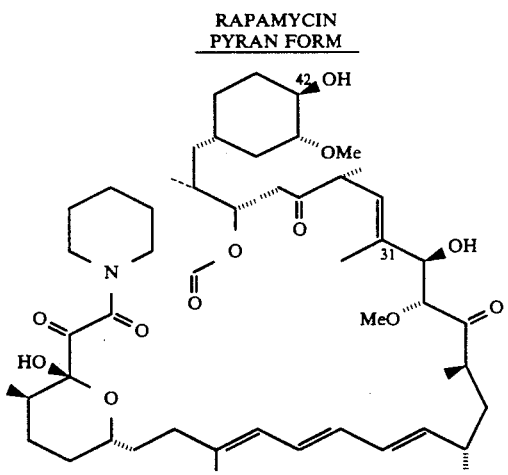

and are prepared from rapamycin or its derivatives by treatment with a strong base in an aprotic media or by isolation from the culture media in which rapamycin is produced. These compounds display modified pharmacodynamic behavior and possess immunosuppressive and/or antifungal and/or antitumor and/or antiinflammatory activity in vivo and/or inhibit thymocyte proliferation in vitro and are therefore useful in the treatment of transplantation rejection, autoimmune diseases (i.e. lupus, rheumatoid arthritis, diabetes mellitus, multiple sclerosis), *Candida albicans* infections, and diseases of inflammation.

PRIOR ART

The prior art relates to rapamycin itself (U.S. Pat. No. 3,929,992) and to derivatives of rapamycin, wherein the hydroxyl groups at carbons numbered 31 and 42 are derivatized to form esters and ethers, along with other modifications of rapamycin. Because rapamycin is unstable to aqueous base solution and the primary mode of decomposition is believed to occur by nucleophilic attack on the electrophilic carbonyl α to the amide of the pyran form of rapamycin; the oxepane analogues, where the carbonyls are less electrophilic, are more stable and thus more potent than the pyran form of rapamycin and display modified pharmacodynamic behavior.

An example of the preparation of compounds of formula I, wherein $R^1$ and $R^2$ are hydrogen, is described below.

EXAMPLE 1

Rapamycin (1.0 g, 1.09 mmol) was dissolved in THF (50 mL), cooled to 78° C. and treated with benzyl magnesium chloride (2.5 mL of 2M solution in THF, 5 mmol). The reaction mixture was warmed to room temperature, stirred for 30 minutes and partitioned between 2N HCl (50 mL) and ethyl acetate (60 mL). The organic layer was washed with brine (50 mL), dried (MgSO$_4$) and concentrated to an oil. The product was chromatographed on a Dynamax ® 60 C$_{18}$ column (41.4 mm ID×30 cm length) using a linear gradient from 100% A (0.1% TFA and 5% acetonitrile in water) to 100% B (pure acetonitrile) over 120 minutes at 25 mL/min. The product elutes in 108 minutes. $^{13}$C-NMR (DMSO-d$_6$) d 210.94, 210.71, 209.39, 208.95, 208.30, 208.09, 170.17, 169.60, 167.63, 167.45, 139.05, 138.36, 138.09, 137.13, 137.07, 136.45, 133.01, 132.29, 130.51, 129.52, 128.52, 127.17 (2C), 126.73, 125.35, 124.19, 98.46, 97.95, 85.81, 85.22, 83.83, 83.75, 82.98, 82.39, 76.12, 75.92, 73.80, 73.22, 73.15, 73.09, 72.70, 71.69, 57.18, 56.89, 56.71, 56.69, 55.79, 55.24, 54.99, 51.19, 45.12, 42.75 (2C), 42.06, 40.95, 40.82, 40.73, 40.33, 39.62, 38.64, 38.52, 37.78, 35.69, 35.49, 35.35, 34.46, 33.92, 33.18, 32.94, 32.79 (2C), 32.72, 32.59, 32.18, 31.30, 31.13, 30.99, 27.18, 25.99, 24.75, 24.20, 21.52 (2C), 21.28, 20.54, 20.46 (2C), 16.94, 16.82 (2C), 16.79 (2C), 15.98, 15.53, 15.43, 14.90, 14.74, 13.69, 13.64, 13.43, 13.30, 10.58, 10.30.

The pharmaceutically acceptable salts may be formed from inorganic cations such as sodium, potassium, and the like.

The compounds of this invention possess immunosuppressive and/or antifungal and/or antitumor and/or antiinflammatory activity in vivo and/or inhibit thymocyte proliferation in vitro and are therefore useful in the prevention and treatment of transplant rejection such as heart, kidney, liver, bone marrow, and skin transplants; graft versus host disease; autoimmune and proliferative diseases such as systemic lupus erythematosus, rheumatoid arthritis, type 1 diabetes, multiple sclerosis, glomerular nephritis, Hashimoto's thyroiditis, myasthenia gravis, uveitis and psoriasis; fungal infections and diseases of inflammation such as dermatitis, eczema, seborrhea and inflammatory bowel disease.

The immunosuppressive effects of the compounds of this invention were evaluated in an in vitro comitogen-induced thymocyte proliferation test procedure to measure lymphocyte proliferation (LAF) and in two in vivo standard pharmacological test procedures. The first in vivo procedure was a popliteal lymph node (PLN) test procedure which measured the effect of compounds of this invention on a mixed lymphocyte reaction and the second in vivo procedure evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice were cultured for 72 hours with PHA and IL-1 and pulsed with tritiated thymidine during the last six hours. Cells are cultured with and without various concentrations of rapamycin, cyclosporin A, or test compound. Cells are harvested and incorporated; radioactivity is determined. Inhibition of lymphoproliferation is assessed in percent change in counts per minute from non-drug treated controls. The results are expressed by the following ratio:

$$\frac{^3\text{H-control thymus cells} - \text{H}^3\text{-rapamycin-treated thymus cells}}{^3\text{H-control thymus cells} - \text{H}^3\text{-test compound-treated cells}}$$

LAF ASSAY RESULT FOR COMPOUND OF EXAMPLE 1
PERCENT CHANGE FROM CONTROL
(mitrogen + 0μM drug added)

| drug conc. | 1μM | 0.1μM | 10nM | 3nM | 1nM | 0.1nM | Non LIN IC 50 |
|---|---|---|---|---|---|---|---|
| Drug + IL-1B | −96 | −93 | −40 | −8 | 2 | 4 | 13.0 nM |

A mixed lymphocyte reaction (MLR) occurs when lymphoid cells from genetically distinct animals are combined in tissue culture. Each stimulates the other to undergo blast transformation which results in increased DNA synthesis that can be quantified by the incorporation of tritiated thymidine. Since stimulating a MLR is a function of disparity at Major Histocompatibility antigens, an in vivo popliteal lymph node (PLN) test procedure closely correlates to host vs. graft disease. Briefly, irradiated spleen cells from BALB/c donors are injected into the right hind foot pad of recipient C3H mice. The drug is given daily, p.o. from Day 0 to Day 4. On Day 3 and Day 4, tritiated thymidine is given i.p., b.i.d. On Day 5, the hind popliteal lymph nodes are removed and dissolved, and radioactivity counted. The corresponding left PLN serves as the control for the PLN from the injected hind foot. Percent suppression is calculated using the non-drug treated animals as allogenic control.

$$\frac{^3H\text{-}PLN \text{ cells control } C3H \text{ mouse} - {}^3H\text{-}PLN \text{ cells rapamycin-treated } C3H \text{ mouse}}{^3H\text{-}PLN \text{ cells control } C3H \text{ mouse} - 3H\text{-}PLN \text{ cells test compound-treated } C3H \text{ mouse}}$$

The second in vivo test procedure is designed to determine the survival time of pinch skin graft from male DBA/2 donors transplanted to male BALB/c recipients. The method is adapted from Billingham R. E. and Medawar P. B., J. Exp. Biol. 28:385–402, (1951). Briefly, a pinch skin graft from the donor is grafted on the dorsum of the recipient as a homograft, and an autograft is used as control in the same region. The recipients are treated with either varying concentrations of cyclosporin A as test control or the test compound, intraperitoneally. Untreated recipients serve as rejection control. The graft is monitored daily and observations are recorded until the graft becomes dry and forms a blackened scab. This is considered as the rejection day. The mean graft survival time (number of days ± S.D.) of the drug treatment group is compared with the control group.

Based on the results of these standard pharmacological test procedures, the compounds of this invention are useful in the prevention and treatment of transplant rejection such as heart, kidney, liver, bone marrow, and skin transplants, graft versus host disease; autoimmune and proliferative diseases such as, systemic lupus erythematosus, rheumatoid arthritis, type 1 diabetes, multiple sclerosis, glomerular nephritis, Hashimoto's thyroiditis, myasthenia gravis, uveitis and psoriasis; diseases of inflammation such as dermatitis, eczema, seborrhea and inflammatory bowel disease; and fungal infections.

The compounds of this invention may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

What is claimed is:

1. A compound of formula (I)

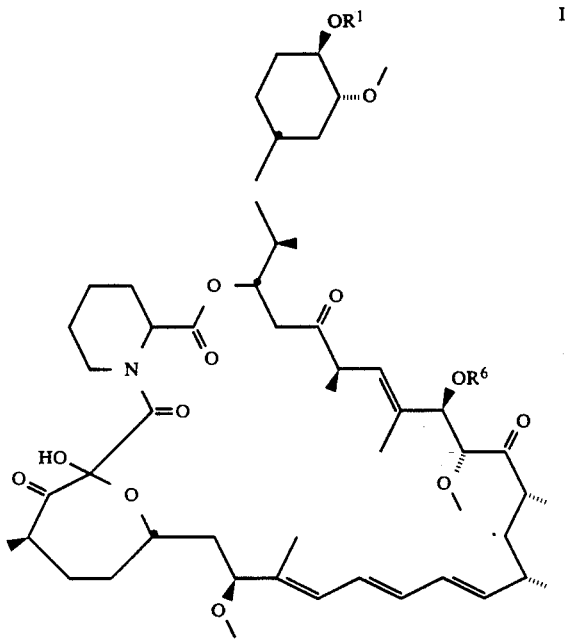

wherein $R^1$ and $R^2$ are selected from the group consisting of hydrogen, alkanoyl, sulfonyl or alkyl containing 1 to 6 carbon atoms or a pharmaceutically acceptable salt thereof.

2. A compound of claim 1 wherein $R^1$ and $R^2$ are hydrogen or a pharmaceutically acceptable salt thereof.

3. A compound of claim 1 wherein $R^1$ and $R^2$ are alkanoyl or a pharmaceutically acceptable salt thereof.

4. A compound of claim 1 wherein $R^1$ and $R^2$ are sulfonyl or a pharmaceutically acceptable salt thereof.

5. A compound of claim 1 wherein $R^1$ and $R^2$ are alkyl containing 1 to 6 carbon atoms or a pharmaceutically acceptable salt thereof.

* * * * *